(12) United States Patent
Park et al.

(10) Patent No.: US 7,892,595 B2
(45) Date of Patent: Feb. 22, 2011

(54) IMPLANTABLE DEVICE COATING SYSTEM AND METHOD

(75) Inventors: Eunsung Park, Plymouth, MN (US); Jeffrey Allen, Santa Rosa, CA (US)

(73) Assignee: Medtronic Vascular, Inc, Santa Rosa, CA (US)

( * ) Notice: Subject to any disclaimer, the term of this patent is extended or adjusted under 35 U.S.C. 154(b) by 721 days.

(21) Appl. No.: 11/673,441

(22) Filed: Feb. 9, 2007

(65) Prior Publication Data

US 2008/0195197 A1  Aug. 14, 2008

(51) Int. Cl.
*A61L 33/00* (2006.01)
(52) U.S. Cl. .......................... 427/2.25; 259/1; 427/2.1; 427/2.24; 427/430.1; 427/435; 427/443.2
(58) Field of Classification Search ............... 259/1; 427/2.25
See application file for complete search history.

(56) References Cited

U.S. PATENT DOCUMENTS

| | | | |
|---|---|---|---|
| 3,614,069 A * | 10/1971 | Murry | ........................ 366/119 |
| 5,562,729 A | 10/1996 | Purdy et al. | |
| 6,321,109 B2 | 11/2001 | Ben-Haim et al. | |
| 6,544,582 B1 | 4/2003 | Yoe | |
| 6,730,349 B2 | 5/2004 | Schwarz et al. | |
| 6,767,637 B2 | 7/2004 | Park et al. | |
| 6,821,549 B2 | 11/2004 | Jayaraman | |
| 7,128,387 B2 | 10/2006 | Takiguchi | |
| 7,131,599 B2 | 11/2006 | Katase | |
| 2002/0082543 A1 | 6/2002 | Park et al. | |
| 2004/0215313 A1 | 10/2004 | Cheng | |
| 2005/0107870 A1 | 5/2005 | Wang et al. | |
| 2005/0149080 A1 | 7/2005 | Hunter et al. | |
| 2005/0220848 A1 | 10/2005 | Bates | |
| 2006/0216403 A1 | 9/2006 | Hayes | |
| 2006/0228464 A1 | 10/2006 | Larson et al. | |
| 2006/0276884 A1 | 12/2006 | Lye et al. | |

FOREIGN PATENT DOCUMENTS

| EP | 0953320 | * | 3/1999 |
|---|---|---|---|
| EP | 0953320 | | 11/1999 |

OTHER PUBLICATIONS

Fisher, Wayne, << Vacuum Impregnation : An Alternative Metho—Electronic Component Sealing Technique << http://finadarticle.com/p/articles/mi_m0HRR/is_2001_Spring/ai_75532385/print.

* cited by examiner

*Primary Examiner*—Michael Barr
*Assistant Examiner*—Andrew Bowman

(57) ABSTRACT

An implantable device coating system method includes providing the implantable device having an exterior surface, the exterior surface including a plurality of pores in fluidic communication with an ambient environment. The method further includes applying a coating including a therapeutic solution to the exterior surface and the pores, and vibrating the implantable device with a sonic wave for a predetermined time using at least one predetermined frequency.

18 Claims, 7 Drawing Sheets

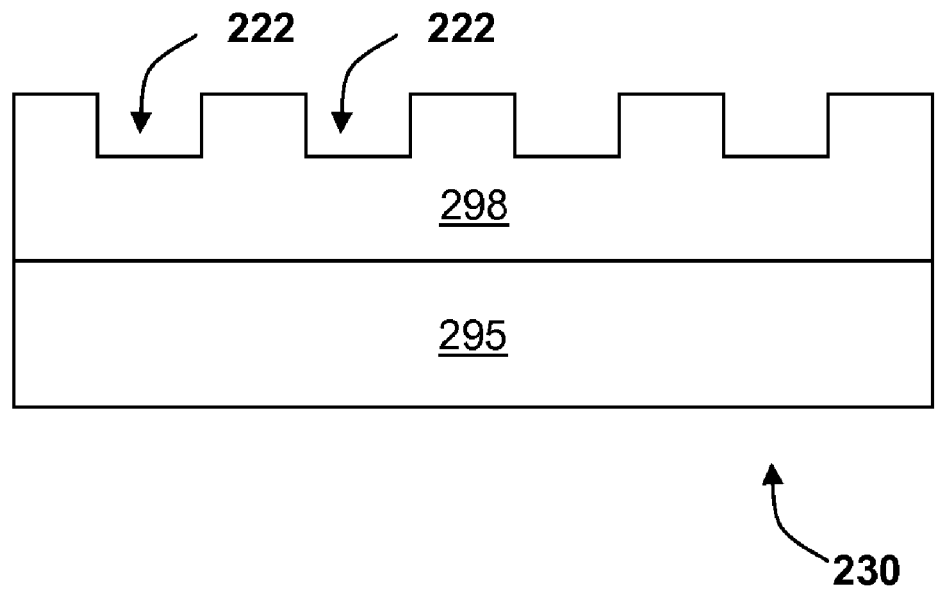

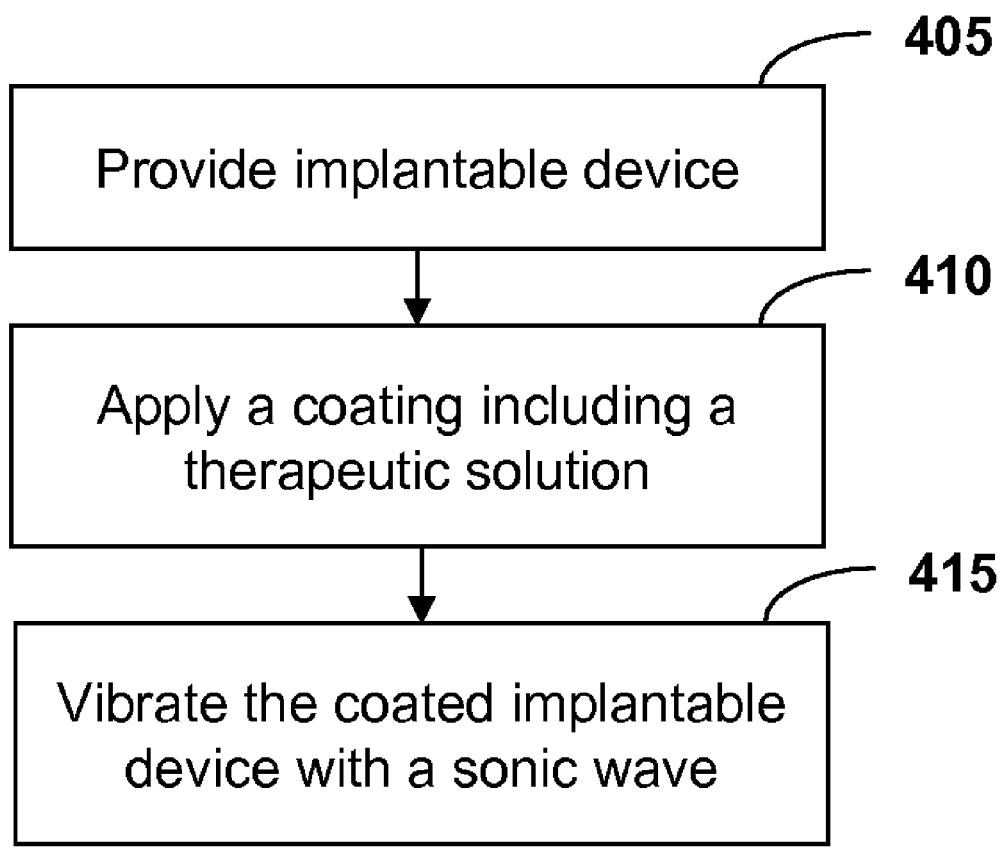

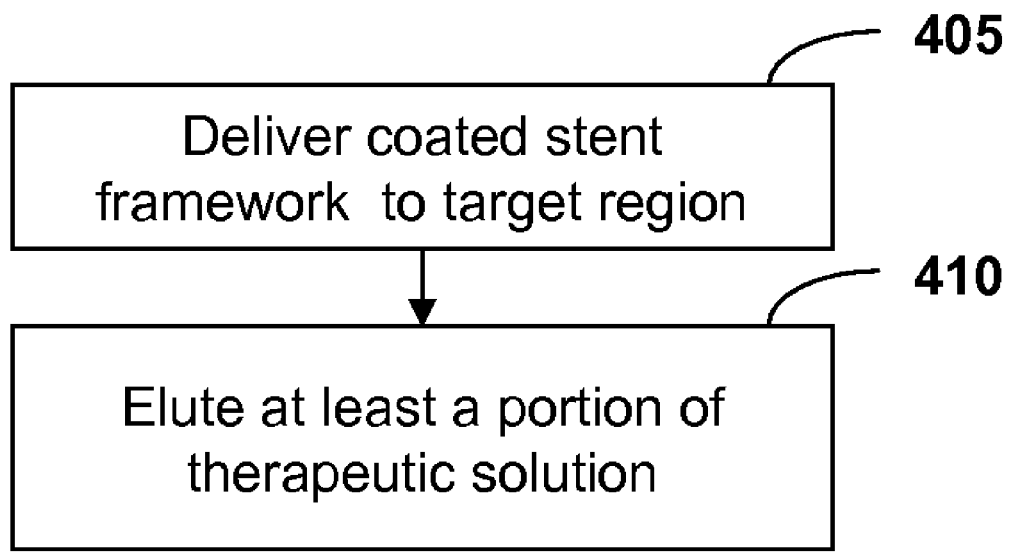

IMPLANTABLE DEVICE COATING SYSTEM AND METHOD

TECHNICAL FIELD

The technical field of this disclosure is medical implantable device coating methods, particularly, a system and method for coating an implantable device with fewer trapped gas bubbles.

BACKGROUND OF THE INVENTION

Wide ranges of medical treatments have been developed using implantable devices such as endoluminal prostheses, which are medical devices adapted for temporary or permanent implantation within a body lumen, including naturally occurring and artificially made lumens. Examples of lumens in which endoluminal prostheses may be implanted include arteries such as those located within coronary, mesentery, peripheral, or cerebral vasculature; veins; gastrointestinal tract; biliary tract; urethra; trachea; hepatic shunts; and fallopian tubes. Various types of endoluminal prostheses have also been developed with particular structure to modify the mechanics of the targeted luminal wall.

Stents are one example of an endoluminal prosthesis. Stents are generally cylindrical shaped devices that are radially expandable to hold open a segment of a blood vessel or other anatomical lumen after implantation into the body lumen. Stents have been developed with coatings to deliver drugs or other therapeutic agents. Various types of stents are in use, including balloon expandable and self-expanding stents. Balloon expandable stents generally are conveyed to the area to be treated on balloon catheters or other expandable devices. For insertion, the stent is positioned in a compressed configuration along a delivery device. The stent may be fixed to a balloon that is folded or otherwise wrapped about a guide catheter that is part of the delivery device. After the stent is positioned across a lesion, the stent is expanded by the delivery device. For a self-expanding stent, a sheath is retracted allowing expansion of the stent.

Stents are used in conjunction with balloon catheters in a variety of medical therapeutic applications including intravascular angioplasty. For example, a balloon catheter is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Unfortunately, significant proportions of treated vessels re-narrow or collapse soon after the procedure.

To prevent acute vessel narrowing or collapse, short flexible cylinders, or stents, constructed of metal or various polymers are implanted within the vessel to maintain lumen diameter. The stents acts as a scaffold to support the lumen in an open position. Balloon-expandable stents are mounted on a collapsed balloon at a diameter smaller than when the stents are deployed. Stents can also be self-expanding, growing to a final diameter when deployed without mechanical assistance from a balloon or like device.

Stent insertion may cause undesirable reactions such as inflammation, infection, thrombosis, and proliferation of cell growth that occludes the passageway. Stents have been used with coatings to deliver drugs or other therapeutic agents to the site of the stent and assist in preventing these conditions. In some drug delivery stents, a drug coating is applied to a stent framework. The coating can be applied as a liquid containing the drug or other therapeutic agent dispersed in a polymer/solvent matrix. The liquid coating then dries to a solid coating upon the stent. The liquid coating can be applied by dipping or spraying the stent while spinning or shaking the stent to achieve a uniform coating. Combinations of the various application techniques can also be used.

One problem that has arisen with coated stents is increasing the volume of therapeutic solutions contained on the stent. Often pores or nanopores in the surface of the stent are used to increase the volume of therapeutic solution held by the stent. However, gas bubbles can be trapped in the pores during the coating process. This is particularly true when the pores are micropores or nanopores in the stent surface. The gas bubbles cling to the small pores, and the surface tension of the coating can trap the gas bubble within the nanopore. The gas bubbles in the pores reduce the pore volume available to hold a therapeutic agent, reducing the amount of therapeutic agent that can be dispensed to the patient. This additionally increases the uncertainty in the amount of therapeutic agent actually loaded in the stent and the uncertainty of the amount of therapeutic agent actually dispensed to the patient.

It would be desirable to have an implantable device coating system and method that would overcome the above disadvantages.

SUMMARY OF THE INVENTION

One aspect of the present invention provides an implantable device coating method that includes providing the implantable device having an exterior surface, the exterior surface including a plurality of pores in fluidic communication with an ambient environment. The method further includes applying a coating including a therapeutic solution to the exterior surface and the pores, and vibrating the implantable device with a sonic wave for a predetermined time using at least one predetermined frequency.

Another aspect of the present invention provides a system for coating an implantable device. The system includes the implantable device having an exterior surface and pores in the exterior surface and means for applying a coating including a therapeutic solution to the exterior surface and the pores. The system further includes means for vibrating the implantable device with a sonic wave for a predetermined time using at least one predetermined frequency.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIG. 2B is a cross-sectional view of a coated stent framework, in accordance with one embodiment of the current invention;

FIG. 4 is an flow diagram of a method for loading an implantable device with a therapeutic coating, in accordance with one aspect of the invention;

FIG. 6 is a flow diagram of a method of applying a treating a vascular condition, in accordance with one embodiment of the current invention.

DETAILED DESCRIPTION

The invention will now be described by reference to the drawings wherein like numbers refer to like structures.

Figure 1:
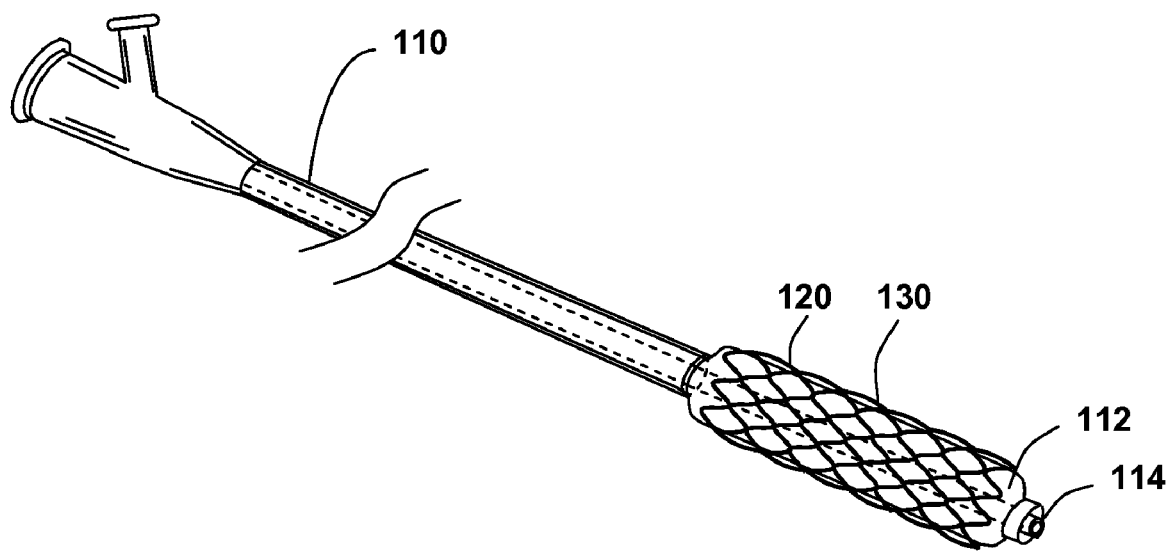
FIG. 1 is an illustration of a system for treating a vascular condition including a stent coupled to a catheter, in accordance with one embodiment of the current invention.

FIG. 1 shows an illustration of a system for treating a vascular condition, comprising a stent coupled to a catheter, in accordance with one embodiment of the present invention at 100. Stent with catheter 100 includes a stent 120 coupled to a delivery catheter 110. Stent 120 includes a stent framework 130. In one embodiment, at least one drug coating, or a drug-polymer layer, is applied to a surface of the stent framework. Stent 120 includes a stent framework with a plurality of pores disposed on an outer surface of the stent framework and a coating disposed over the stent framework and throughout the plurality of pores such that the coating includes a concentration of gas bubbles below 5% by volume. The pores, in one embodiment, are nanopores. In another embodiment, the pores are micropores. The pores can extend into the surface of the implantable device substantially perpendicularly, or substantially tortuously.

Insertion of stent 120 into a vessel in the body helps treat, for example, heart disease, various cardiovascular ailments, and other vascular conditions. Catheter-deployed stent 120 typically is used to treat one or more blockages, occlusions, stenoses, or diseased regions in the coronary artery, femoral artery, peripheral arteries, and other arteries in the body. Treatment of vascular conditions may include the prevention or correction of various ailments and deficiencies associated with the cardiovascular system, the cerebrovascular system, urinogenital systems, biliary conduits, abdominal passageways and other biological vessels within the body.

Catheter 110 of an exemplary embodiment of the present invention includes a balloon 112 that expands and deploys the stent within a vessel of the body. After positioning stent 120 within the vessel with the assistance of a guide wire traversing through a guide wire lumen 114 inside catheter 110, balloon 112 is inflated by pressurizing a fluid such as a contrast fluid or saline solution that fills a tube inside catheter 110 and balloon 112. Stent 120 is expanded until a desired diameter is reached, and then the contrast fluid is depressurized or pumped out, separating balloon 112 from stent 120 and leaving the stent 120 deployed in the vessel of the body. Alternately, catheter 110 may include a sheath that retracts to allow expansion of a self-expanding version of stent 120.

The stent 120 can be any variety of implantable devices capable of carrying a coating known in the art and being expandable with a balloon or self expandable to hold open a lumen. The stent has a plurality of interconnecting struts and an end cap at each end joining the ends of the interconnecting struts. The stent has an exterior surface including an outer surface and an inner surface. In one embodiment, the outer surface of the stent includes pores. In one embodiment, the inner surface of the stent includes pores. Other pores or surface openings such as channels or dimples can be manufactured using other methods know in the art. Alternatively, the stent can be any other appropriate drug delivery system, such as a drug delivery balloon.

Figure 2A:
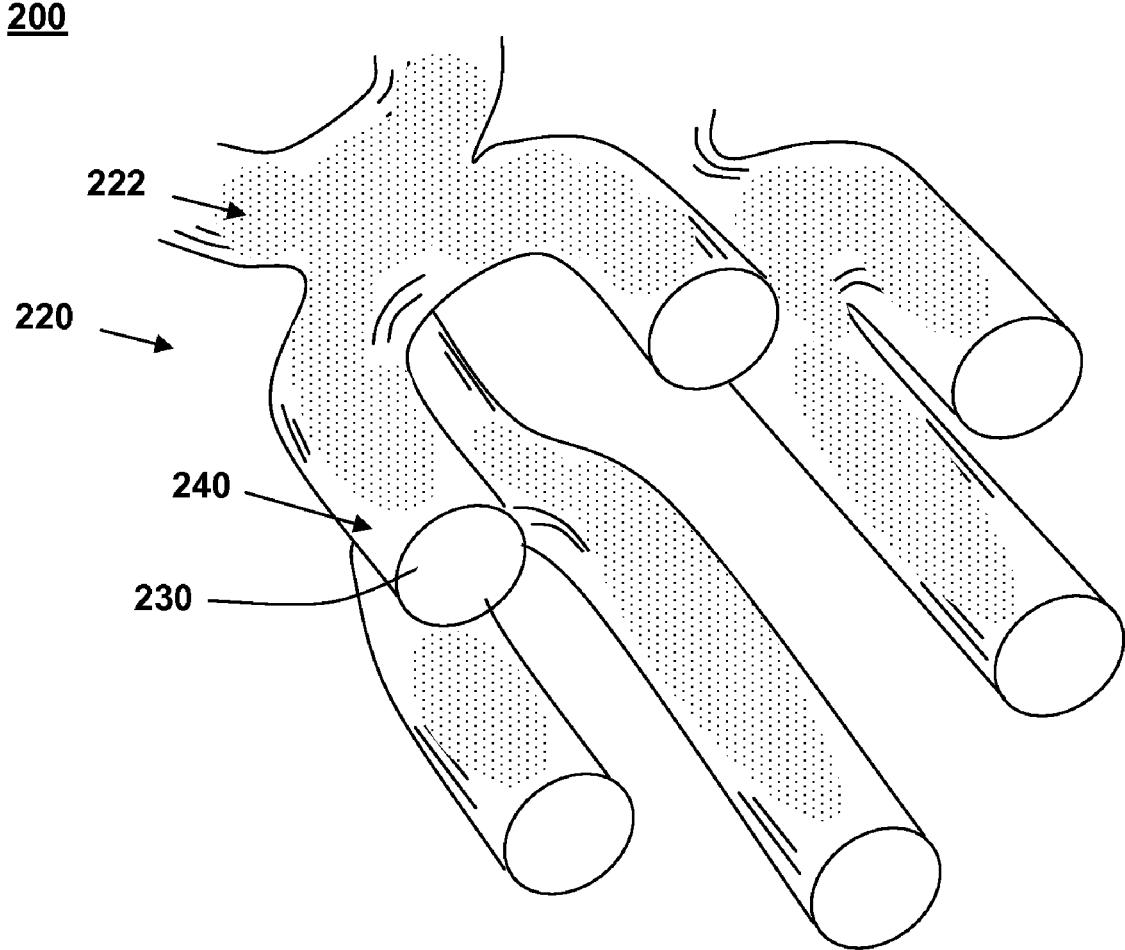
FIG. 2A is a cross-sectional perspective view of a coated stent framework, in accordance with one embodiment of the current invention.

FIG. 2A shows a cross-sectional perspective view of a stent, in accordance with one embodiment of the present invention at 200. Stent 220 includes a stent framework 230.

Stent framework 230 comprises any appropriate material, such as a polymer, a metal, and a metallic base formed of magnesium, cobalt-chromium, stainless steel, nitinol, tantalum, MP35N alloy, platinum, titanium, a chromium-based alloy, a suitable biocompatible alloy, a suitable biocompatible material, a biocompatible polymer, or a combination thereof.

In one embodiment, a drug coating 240 is disposed on stent framework 230. In other embodiments, at least one coating layer is disposed over the stent framework, and can envelop or surround the drug coating. For example, drug coating 240 includes at least a first therapeutic agent. In one embodiment, the coating layers include magnesium. In one embodiment, the coating layers are sputter coats. In other embodiments, the magnesium coating is applied using another appropriate technique, such as vacuum deposition, dipping, ultrasonic spraying, electrostatic spraying, or the like. In one embodiment, the coating layer is a topcoat.

Although illustrated with one set of drug layers and coating layers, multiple sets of drug and coating layers may be disposed on stent framework 230. For example, ten sets of layers, each layer on the order of 0.1 micrometers thick, can be alternately disposed on stent framework 230 to produce a two-micrometer thick coating. In another example, twenty sets of layers, each layer on the order of 0.5 micrometers thick, can be alternately disposed on stent framework 230 to produce a twenty-micrometer thick coating. The drug layers and the coating layers need not be the same thickness, and the thickness of each may be varied throughout drug coating 240. In one example, at least one drug layer is applied to an outer surface of the stent framework. The drug layer can comprise a first therapeutic agent such as camptothecin, rapamycin, a rapamycin derivative, or a rapamycin analog. In another example, at least one coating layer comprises a magnesium layer of a predetermined thickness. In one embodiment, the thickness of the magnesium coating is selected based on expected leaching rates, while in other embodiments, the thickness is selected based on the drug maintained in place between the magnesium alloy stent framework surface and the magnesium layer. In another embodiment, the thickness of the magnesium layer is variable over the length of the stent framework. Drug or magnesium elution refers to the transfer of a therapeutic agent from drug coating 240 to the surrounding area or bloodstream in a body. The amount of drug eluted is determined as the total amount of therapeutic agent excreted out of drug coating 240, typically measured in units of weight such as micrograms, or in weight per peripheral area of the stent.

FIG. 2B illustrates the stent 200 of FIG. 2A with a plurality of pores 222 within the surface of the stent. In one embodiment, pores 222 are nanopores. In one embodiment, the pores 222 include a diameter less than 100 nanometers.

Figure 3:
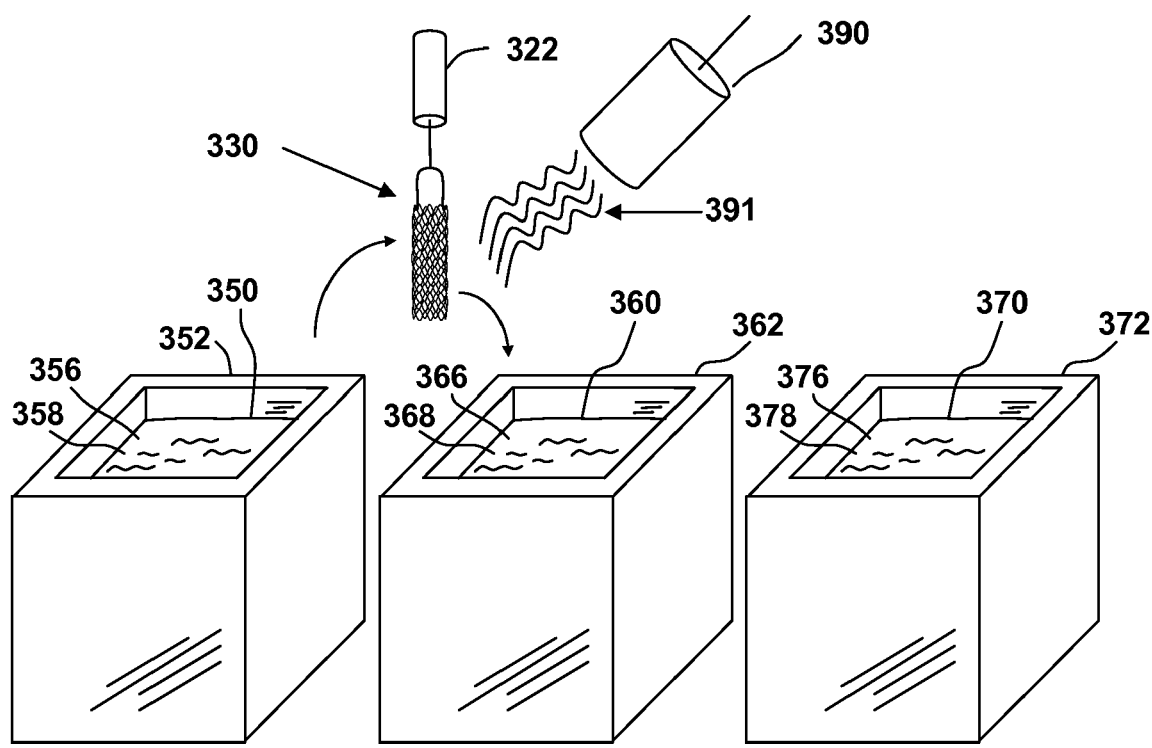
FIG. 3 is an illustration of a system for applying a drug coating on a stent, in accordance with one embodiment of the current invention.

FIG. 3 shows an illustration of an example system for applying a drug coating on a stent, in accordance with one embodiment of the current invention at 300. Drug coating system 300 includes a first solution 350 in a first tank 352, a second solution 360 in a second tank 362, and a mechanism 322 such as a mandrel, a clamp, or a tether for holding and transporting stents in and out of a tank either manually or automatically. Multiple stent frameworks 330 are readily accommodated for dipping and drying in a batch or continuous batch process.

For example, first solution 350 includes a first therapeutic agent 356, and a first solvent 358. Stent framework 330 can be dipped into first solution 350 and dried, for example, by positioning dipped stent framework 330 in air or in an oven and evaporating first solvent 358 to form a drug layer. Minimizing the solids content of first solution 350 can lower the viscosity, so that uniform coating and minimal or no bridging occurs across the apertures of stent framework 330.

Second solution 360 includes second therapeutic agent and a second solvent 368. Stent framework 330 with the first laminated drug layer can be dipped into second solution 360 and dried, for example, by positioning dipped stent framework 330 in an oven or in air for high throughput and evaporating second solvent 368 to form a therapeutic agent layer. Second solution 360 may include a second therapeutic agent 366 dissolved into second solvent 368. Low viscosity for minimizing bridging and webbing across the apertures of stent framework 330 can be obtained by minimizing the solids content of second solution 360.

A third solution 370 in a third tank 372 includes a third solvent 378 in certain embodiments. Third solution 370 may include a third therapeutic agent 376 dissolved in third solvent 378. In one example, third solvent 378 is the same as first solvent 358, and third therapeutic agent 376 is the same as first therapeutic agent 356, though at a higher or a lower concentration than first therapeutic agent 356 in first solution 350. In this case, the concentration of third therapeutic agent 376 disposed on stent framework 330 can be higher or lower than previously dipped and dried drug layers. The concentration of first therapeutic agent 356 in the drug layers can be modulated to provide a predetermined drug-release profile.

In another example, third solvent 378 is the same as second solvent 368, and third therapeutic agent 376 is the same as second therapeutic agent 366 though at a higher or a lower concentration than second therapeutic agent 366 in second solution 360. The concentration of third therapeutic agent 376 disposed on stent framework 330 can be higher or lower than previously dipped and dried barrier layers, so that the concentration of second therapeutic agent 366 in the barrier layers can be modulated to provide a predetermined drug-release profile for second therapeutic agent 366 from a coated stent when deployed in a body.

In addition to the dipping tanks, the system further includes a sonic wave device 390. Device 390 generates a directionally-focused plurality of sound waves 391 at a selected frequency and amplitude. Any appropriate commercially available sonic wave device can be used. In one embodiment, the device is a sonic transducer. The sonic wave device 390 applies directionally-focused plurality of sound waves 391 after applying the coating and while the implantable device is substantially surrounded by air.

FIG. 4 illustrates one embodiment of a method 400 for loading an implantable device with a therapeutic solution, in accordance with one aspect of the invention. Method 400 begins at 405 by providing the implantable device. The implantable device includes an exterior surface that has a plurality of pores in fluidic communication with an environment. Gases within the environment enter the pores and exit the pores, responsive to air currents within the environment.

A coating is applied to the implantable device at block 410. The coating includes a therapeutic solution and covers the implantable device. At least a portion of the coating enters at least one of the pores. For example, the therapeutic solution includes a therapeutic substance and a solvent. In other embodiments, the therapeutic solution includes a therapeutic substance, solvent, and at least one polymer. In certain embodiments, the therapeutic substance is a drug such as an antirestenotic agent such as rapamycin, a rapamycin derivative, or a rapamycin analog to prevent or reduce the recurrence of narrowing and blockage of the bodily vessel, an anti-cancer drug such as camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, or a combination thereof. The coating can be applied by any appropriate technique, including dipping, spraying, sputtering, vacuum deposition, or the like.

Figure 5A:
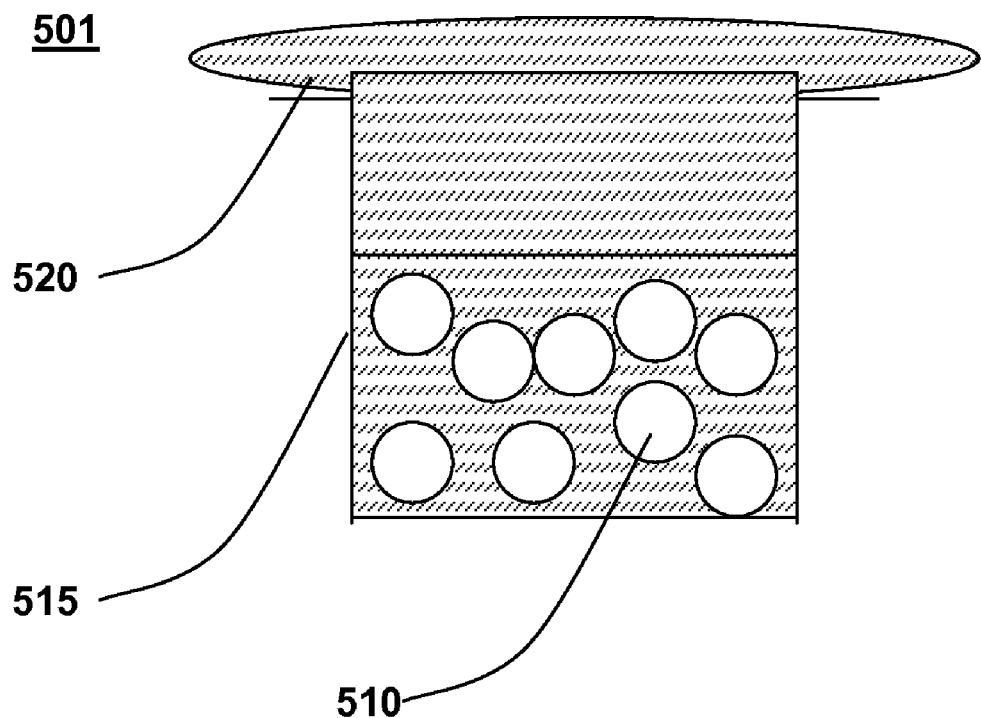
FIG. 5A is a view of a pore including a concentration of gas bubbles, in accordance with one embodiment of the current invention.
Figure 5B:
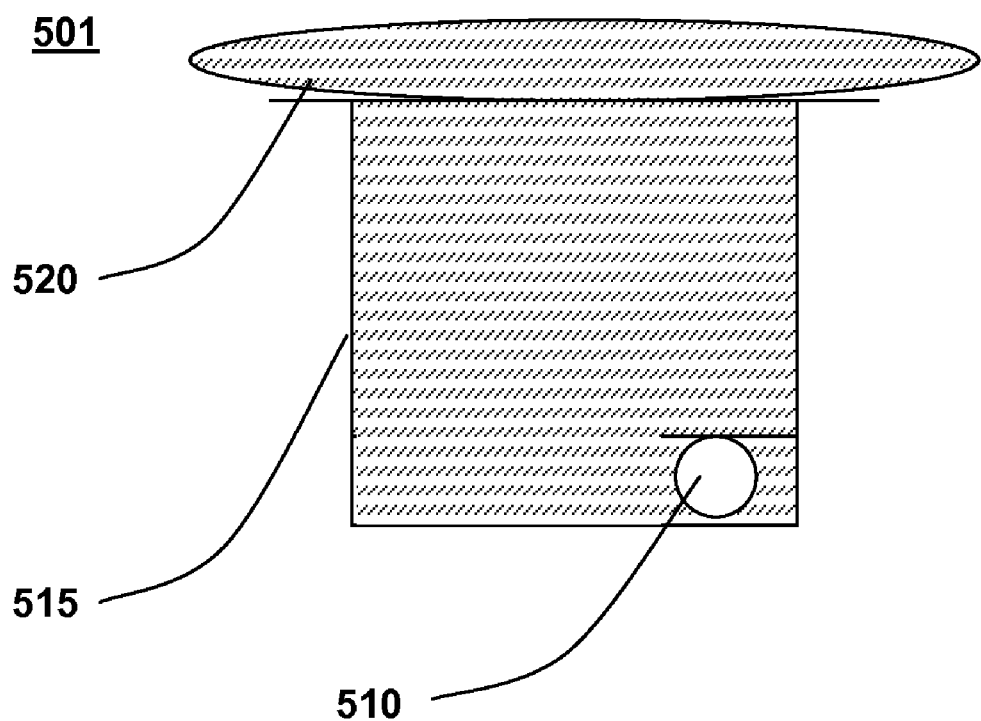
FIG. 5B is a view of the pore of FIG. 5 with the concentration decreased.

As the coating is applied to the implantable device, at least one air bubble is trapped within a nanopore by the coating. For example, the surface tension of the coating may be sufficiently high as to prevent the air bubble within the nanopore from mixing freely with an environment not constrained by the walls and surfaces of the nanopore. FIG. 5 illustrates gas bubbles 510 disposed within nanopore 515. Gas bubbles 510 are trapped in the nanopore by coating 520.

With the coating at least partially applied, the implantable device is vibrated with a sonic wave, such as wave 391, for a predetermined time using at least one predetermined frequency at block 415. In one embodiment, the implantable device can be vibrated by the sonic wave while the coating is being applied. In another embodiment, the implantable device is vibrated after the coating has been fully applied. In one embodiment, the implantable device is vibrated while the coating remains wet. A sonic wave is any directable energy. In one embodiment, the frequency of the sonic wave is within the hearing range of a human. In one embodiment, the vibration of the implantable device resulting from the sonic wave induces fluid flow within the nanopore. In one embodiment, the fluid flow is sufficient to disturb the surface tension of the coating, releasing the gas bubbles. In one embodiment, the environment surrounding the implantable device is controlled to a negative pressure to further enhance the release of gas bubbles. In one embodiment, the negative pressure can be applied in a sealed chamber. In one embodiment, the implantable device is moved to the sealed chamber to be vibrated after the coating is applied to the implantable device. In another embodiment, the sonic wave is directed through a fluid bath surrounding the implantable device to vibrate the implantable device while the device is being dipped in the fluid bath. In another example, the energy transmitted by the sonic wave is transferred from the sonic wave device via the sonic wave to the implantable device to the wall of the nanopore, and to the fluid disposed within the nanopore to interact with the bubble to migrate the bubble out of the nanopore or to break the bubble up.

The sonic wave can be directed from a single sonic wave, or from multiple sonic waves. The sonic waves can be directed at the implantable device from a plurality of angles and either simultaneously or sequentially. For example, one sonic wave is directed at the implantable device from an angle perpendicular to the axis defined by a lumen of the implantable device, while other sonic waves can be directed at angles oblique to that axis. The sonic wave can be tightly directed to focus on a particular area of the implantable device or simply directed in the general direction of the implantable device.

The sonic wave is pulsed, in one embodiment. In another embodiment, the sonic wave is applied substantially continuously. In one embodiment, the sonic wave is a nanovibrational acoustic wave. In another embodiment, the frequency of the nanovibrational acoustic wave is in the range of about 1 to about 50 megahertz. In another embodiment, the amplitude of the nanovibrational acoustic wave is in the range of about 1 to about 50 nanometers. In yet another embodiment, during the vibration, the implantable device is rotated about at least one axis defined by the implantable device. In other embodiments, the amplitude of the acoustic wave is controlled to exhibit desired properties.

FIG. 6 shows a flow diagram of a method of treating a vascular condition, in accordance with one embodiment of the present invention at 600. Method 600 begins by delivering a stent framework with a plurality of pores covered with a coating including a concentration of gas bubbles less than about 5% by volume to a target region of a vessel at step 605. Once delivered, at least a portion of the therapeutic solution is eluted from the coating, as seen at block 610.

As used herein, the term nanopores is defined as pores having diameters of less than 500 nanometers, and typically having diameters of less than 100 nanometers. In one embodiment, the pores can extend straight into the stent framework, approximately perpendicular to an axis formed by a lumen of the implantable device or stent. In another embodiment, the pores can extend tortuously into the stent framework with reference to the axis. Those skilled in the art will appreciate that the pores can have particular depths and geometries as desired for a particular application. The depths and geometries can be selected to allow a particular release characteristic for a therapeutic agent, for example. In addition, the shape or geometry of the pores can be controlled to affect release characteristics. Additionally, the geometry of each nanopore can vary along the span of a single stent to provide for a plurality of release characteristics.

In one embodiment, the coating includes a therapeutic agent without a polymer carrier. Suitable therapeutic agents include, but are not limited to, antiangiogenesis agents, antiendothelin agents, antimitogenic factors, antioxidants, antiplatelet agents, antiproliferative agents, antisense oligonucleotides, antithrombogenic agents, calcium channel blockers, clot dissolving enzymes, growth factors, growth factor inhibitors, nitrates, nitric oxide releasing agents, vasodilators, virus-mediated gene transfer agents, agents having a desirable therapeutic application, combinations of the above, and the like. Specific example of therapeutic agents include abciximab, angiopeptin, colchicine, eptifibatide, heparin, hirudin, lovastatin, methotrexate, rapamycin, Resten-NG (AVI-4126) antisense compound, streptokinase, taxol, ticlopidine, tissue plasminogen activator, trapidil, urokinase, and growth factors VEGF, TGF-beta, IGF, PDGF, and FGF.

In another embodiment, the coating is a therapeutic agent with a polymer carrier. Suitable polymers include, but are not limited to, urethane, polyester, epoxy, polycaprolactone (PCL), polymethylmethacrylate (PMMA), PEVA, PBMA, PHEMA, PEVAc, PVAc, Poly N-Vinyl pyrrolidone, Poly (ethylene-vinyl alcohol), combinations of the above, and the like. In one embodiment, the coating be removed from the exterior surface of the stent so that the polymer is only found in the pores. The coating can be removed mechanically by methods, or chemically.

For application, the therapeutic agent can be mixed with a solvent to form a therapeutic solution. Suitable solvents include, but are not limited to, acetone, ethyl acetate, tetrahydrofuran (THF), chloroform, N-methylpyrrolidone (NMP), combinations of the above, and the like.

It is important to note that this disclosure and illustrations illustrate specific applications and embodiments of the present invention, and are not intended to limit the scope of the present disclosure or claims to that which is presented therein. Upon reading the specification and reviewing the drawings hereof, it will become immediately obvious to those skilled in the art that many other embodiments of the present invention are possible, and that such embodiments are contemplated and fall within the scope of the presently claimed invention.

While specific embodiments of the invention are disclosed herein, various changes and modifications can be made without departing from the spirit and scope of the invention. The scope of the invention is indicated in the appended claims, and all changes that come within the meaning and range of equivalents are intended to be embraced therein.

The invention claimed is:

1. A method of loading an implantable device with a therapeutic solution comprising:
   providing the implantable device having an exterior surface, the exterior surface including a plurality of pores in fluidic communication with an environment;
   applying a coating including a therapeutic solution to the exterior surface and the pores; and
   vibrating the implantable device with a sonic wave for a predetermined time using at least one predetermined frequency, after applying the coating and while the implantable device is substantially surrounded by air and while the coating material is not dried.

2. The method of claim 1 wherein the vibration induces fluid flow within the pores.

3. The method of claim 1 wherein the application of the coating to the stent traps at least one gas bubble within a pore, and wherein the vibration disrupts the surface tension of the coating to release at least one gas bubble.

4. The method of claim 1 wherein the implantable device is a stent.

5. The method of claim 1 wherein the diameter of the pores is selected from the group consisting of less than 100 nanometers, between 100 and 500 nanometers; between 500 and 1000 nanometers, and greater than 1000 nanometers.

6. The method of claim 1 further comprising applying a negative pressure to the implantable device and coating.

7. The method of claim 6 wherein the negative pressure is applied to the implantable device and coating in a sealed chamber.

8. The method of claim 1 wherein the therapeutic solution consists of a therapeutic agent and a solvent.

9. The method of claim 1 wherein the therapeutic solution consists of a therapeutic agent, a solvent, and a polymer.

10. The method of claim 1 wherein the implantable device defines at least one lumen including an axis and the vibrating further comprises directing the sonic wave substantially perpendicular to the axis.

11. The method of claim 10 further comprising directing a second sonic wave toward the pores at an oblique angle to the axis.

12. The method of claim 1 wherein the vibrating further comprises pulsing the sonic wave.

13. The method of claim 1 wherein the vibrating further comprises varying frequency of the sonic wave.

14. The method of claim 1 wherein the sonic wave is generated by a sonic transducer.

15. The method of claim 1 wherein the sonic wave is a nanovibrational acoustic wave.

16. The method of claim 15 wherein the frequency of the nanovibrational acoustic wave is in the range of about 1 to 50 Megahertz.

17. The method of claim 16 wherein the amplitude of the nanovibrational acoustic wave is in the range of about 1 to 50 nanometers.

18. The method of claim 1 further comprising rotating the implantable device about a longitudinal axis of the implantable device.

* * * * *